(12) United States Patent
Lv et al.

(10) Patent No.: US 7,854,551 B2
(45) Date of Patent: Dec. 21, 2010

(54) X-RAY DETECTING STAND AND X-RAY IMAGING APPARATUS

(75) Inventors: Yong Lv, Beijing (CN); Aimin Yu, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 71 days.

(21) Appl. No.: 12/356,493

(22) Filed: Jan. 20, 2009

(65) Prior Publication Data

US 2009/0190721 A1 Jul. 30, 2009

(30) Foreign Application Priority Data

Jan. 25, 2008 (CN) .................. 2008 1 0009090

(51) Int. Cl.
*H05G 1/64* (2006.01)
(52) U.S. Cl. ..................................... 378/189
(58) Field of Classification Search ................ 378/167, 378/181, 189, 196, 197
See application file for complete search history.

(56) References Cited

U.S. PATENT DOCUMENTS

| | | | |
|---|---|---|---|
| 4,807,272 A | 2/1989 | Guenther et al. | |
| 5,023,899 A * | 6/1991 | Ohlson | 378/196 |
| 5,042,487 A | 8/1991 | Marquardt | |
| 5,305,365 A * | 4/1994 | Coe | 378/37 |
| 5,982,848 A | 11/1999 | Friedrich et al. | |
| 6,065,705 A * | 5/2000 | Schmitt | 242/375.1 |
| 6,282,264 B1 | 8/2001 | Smith et al. | |
| 6,810,108 B2 | 10/2004 | Clark et al. | |
| 6,851,851 B2 | 2/2005 | Smith et al. | |
| 6,935,779 B2 | 8/2005 | Zhang et al. | |
| 6,997,422 B2 | 2/2006 | Sweere et al. | |
| 7,003,070 B1 | 2/2006 | Chen et al. | |
| 7,540,660 B2 * | 6/2009 | Koyanagi | 378/189 |
| 2003/0223549 A1* | 12/2003 | Winsor et al. | 378/189 |

FOREIGN PATENT DOCUMENTS

JP 2005-021233 1/2005

* cited by examiner

*Primary Examiner*—Allen C. Ho
(74) *Attorney, Agent, or Firm*—Armstrong Teasdale LLP

(57) ABSTRACT

An X-ray detecting stand that includes an X-ray detector, a vertical column that supports the X-ray detector so as to be movable, and elevating device for raising and lowering the X-ray detector along the column through a belt, including a balancing mechanism that exerts force, which balances a load by the X-ray detector, to the belt by a clockwork spring. The balancing mechanism has a wire having one end coupled to the belt at the side opposite to the X-ray detector, a wheel that reels up the other end of the wire, and a clockwork spring that applies take-up torque to the wheel.

19 Claims, 6 Drawing Sheets

X-RAY DETECTING STAND AND X-RAY IMAGING APPARATUS

CROSS REFERENCE TO RELATED APPLICATIONS

This application claims the benefit of Chinese Patent Application No. 200810009090.5 filed Jan. 25, 2008, which is hereby incorporated by reference in its entirety.

BACKGROUND OF THE INVENTION

The embodiments described herein relate to an X-ray detecting stand and an X-ray imaging apparatus, and more particularly, to an X-ray detecting stand that can raise and lower an X-ray detector along a vertical column, and an X-ray imaging apparatus having the X-ray stand.

An X-ray imaging apparatus irradiates an X-ray to a patient from an X-ray irradiator, and detects the transmitted X-ray by an X-ray detector so as to form a fluoroscopic image. A subject to be imaged faces the X-ray detector between the X-ray irradiator and the X-ray detector.

Some of the X-ray imaging apparatus have an X-ray stand. The X-ray stand can raise and lower the X-ray detector along a vertical column. By using the X-ray stand, the height of the X-ray detector can be adjusted according to the desired imaged portion (see, for example, Japanese Published Unexamined Patent Application No. 2005-21233 (paragraph number 0010 to 0012, FIG. 1)).

BRIEF DESCRIPTION OF THE INVENTION

In order to reduce the load upon raising and lowering the X-ray detector, the X-ray stand is provided with a counterpoise that balances the load by the X-ray detector. However, it is determined that the use of lead, which is a material of the counterpoise, is inhibited by regulation by law.

Accordingly, an X-ray detecting stand is provided that does not need a counterpoise, which balances the load by the X-ray detector, and an X-ray imaging apparatus having the X-ray stand.

According to a first aspect, an X-ray detecting stand includes an X-ray detector; a vertical column that supports the X-ray detector so as to be movable; elevating device for raising and lowering the X-ray detector along the column through a belt; and a balancing mechanism that exerts force, which balances a load by the X-ray detector, to the belt by a clockwork spring.

In a second aspect, and according to in the first aspect, the balancing mechanism has a first wire having one end coupled to the belt at the side opposite to the X-ray detector; a first wheel that reels up the other end of the first wire; and a first clockwork spring that applies take-up torque to the first wheel.

In a third aspect, and according to the second aspect, the balancing mechanism has a second wire having one end coupled to the belt at the side opposite to the X-ray detector; a second wheel that reels up the other end of the second wire; a second clockwork spring that applies take-up torque to the second wheel; a rotatable axis to which the end of the second clockwork spring opposite to the second wheel is coupled; a ratchet gear having the axis as a rotational axis; a detent that is biased by a spring toward the direction of engaging with the ratchet gear; and a preventing mechanism that prevents the engagement between the detent and the ratchet gear by utilizing a tension of the first wire.

In a fourth aspect, and according to the third aspect, the preventing mechanism has a swing arm to which the detent is mounted; a spring that biases the swing arm toward the ratchet gear; and a returning mechanism that returns the swing arm toward the direction reverse to the ratchet gear by utilizing the tension of the first wire.

In a fifth aspect, and according to the fourth aspect, the returning mechanism has a transition wheel that regulates the direction of the first wire.

In a sixth aspect, and according to the first aspect, the balancing mechanism is provided at the lower part of the column.

In a seventh aspect, and according to the first aspect, the elevating device has a driving mechanism for driving the belt at the upper part of the column.

In an eighth aspect, and according to the seventh aspect, the driving mechanism raises and lowers the X-ray detector through two belts parallel to both side faces of the column.

According to a ninth aspect, an X-ray imaging apparatus includes an X-ray detector; a vertical column that supports the X-ray detector so as to be movable; elevating device for raising and lowering the X-ray detector along the column through a belt; an X-ray irradiator; and a balancing mechanism that exerts force, which balances a load by the X-ray detector, to the belt by a clockwork spring.

In a tenth aspect, and according to the ninth aspect, the balancing mechanism has a first wire having one end coupled to the belt at the side opposite to the X-ray detector; a first wheel that reels up the other end of the first wire; and a first clockwork spring that applies take-up torque to the first wheel.

In an eleventh aspect, and according to the tenth aspect, the balancing mechanism has a second wire having one end coupled to the belt at the side opposite to the X-ray detector; a second wheel that reels up the other end of the second wire; a second clockwork spring that applies take-up torque to the second wheel; a rotatable axis to which the end of the second clockwork spring opposite to the second wheel is coupled; a ratchet gear having the axis as a rotational axis; a detent that is biased by a spring toward the direction of engaging with the ratchet gear; and a preventing mechanism that prevents the engagement between the detent and the ratchet gear by utilizing a tension of the first wire.

In a twelfth aspect, and according to the eleventh aspect, the preventing mechanism has a swing arm to which the detent is mounted; a spring that biases the swing arm toward the ratchet gear; and a returning mechanism that returns the swing arm toward the direction reverse to the ratchet gear by utilizing the tension of the first wire.

In a thirteenth aspect, and according to the twelfth aspect, the returning mechanism has a transition wheel that regulates the direction of the first wire.

In a fourteenth aspect, and according to the ninth aspect, the balancing mechanism is provided at the lower part of the column.

In a fifteenth aspect, and according to the ninth aspect, the elevating device has a driving mechanism for driving the belt at the upper part of the column.

In a sixteenth aspect, and according to the fifteenth aspect, the driving mechanism raises and lowers the X-ray detector through two belts parallel to both side faces of the column.

Described herein are various embodiments of an X-ray detecting stand that includes an X-ray detector, a vertical column that supports the X-ray detector so as to be movable, and elevating device for raising and lowering the X-ray detector along the column through a belt, and has a balancing mechanism that exerts force, which balances a load by the X-ray detector, to the belt by a clockwork spring. Therefore, the embodiments described herein provide an X-ray detecting stand that does not need a counterpoise, which balances the load by the X-ray detector, and an X-ray imaging apparatus having the X-ray stand.

Since the balancing mechanism has a first wire having one end coupled to the belt at the side opposite to the X-ray detector, a first wheel that reels up the other end of the first wire, and a first clockwork spring that applies take-up torque to the first wheel, force that balances the load by the X-ray detector can appropriately be exerted to the belt.

Since the balancing mechanism has a second wire having one end coupled to the belt at the side opposite to the X-ray detector, a second wheel that reels up the other end of the second wire, a second clockwork spring that applies take-up torque to the second wheel, a rotatable axis to which the end of the second clockwork spring opposite to the second wheel is coupled, a ratchet gear having the axis as a rotational axis, a detent that is biased by a spring toward the direction of engaging with the ratchet gear, and a preventing mechanism that prevents the engagement between the detent and the ratchet gear by means of the tension of the first wire, the backup when the first wire is broken is possible.

Since the preventing mechanism has a swing arm to which the detent is mounted, a spring that biases the swing arm toward the ratchet gear, and a returning mechanism that returns the swing arm toward the direction reverse to the ratchet gear by utilizing the tension of the first wire, the engagement between the detent and the ratchet mechanism can easily be prevented.

Since the returning mechanism has a transition wheel that regulates the direction of the first wire, the tension of the first wire can appropriately be utilized.

Since the balancing mechanism is provided at the lower part of the column, the balancing operation can appropriately be performed.

Since the elevating device has a driving mechanism for driving the belt at the upper part of the column, the belt can appropriately be driven.

Since the driving mechanism raises and lowers the X-ray detector through two belts parallel to both side faces of the column, the X-ray detector can appropriately be raised and lowered.

DETAILED DESCRIPTION OF THE INVENTION

Figure 1:
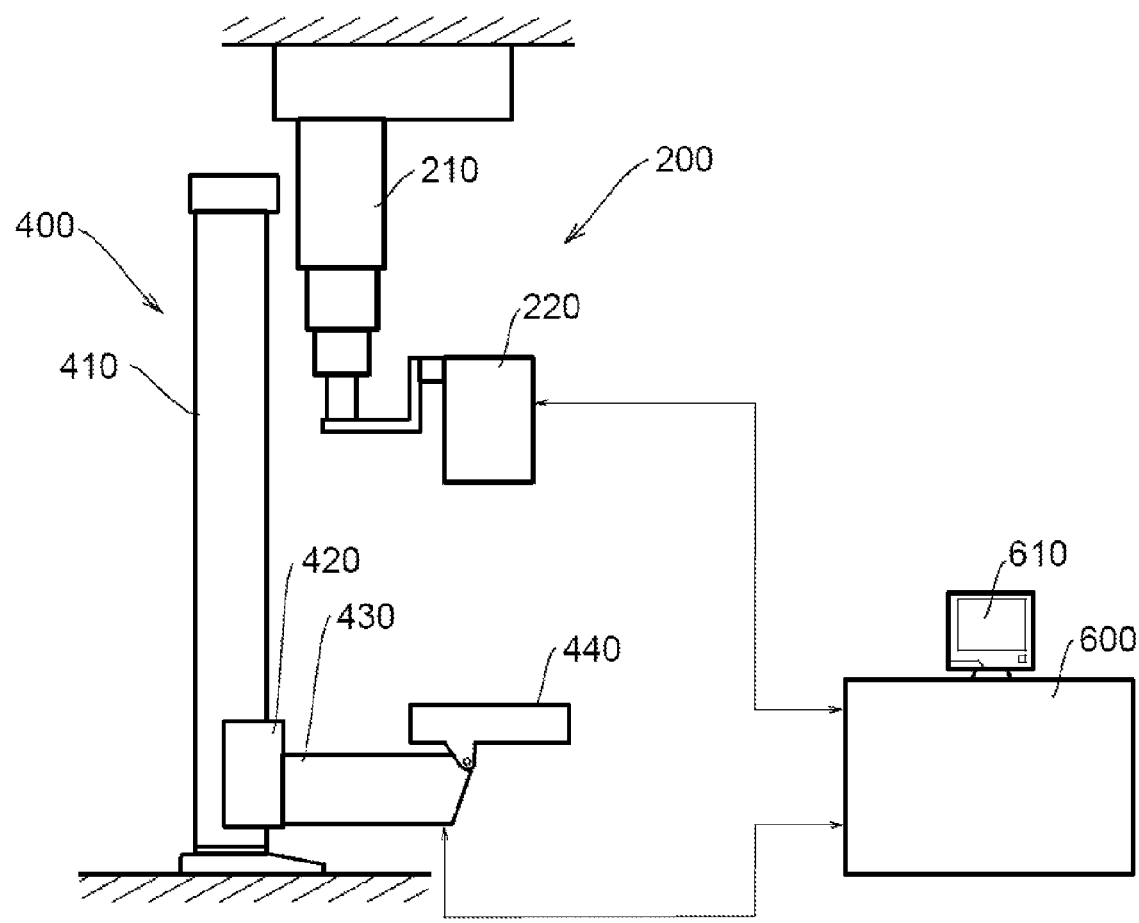
FIG. 1 is a view showing a configuration of an X-ray imaging apparatus according to one example of a best mode for carrying out the present invention.

Various embodiments of the present invention will be explained in detail with reference to the drawings. The present invention is not limited to the embodiments described herein. FIG. 1 schematically shows the configuration of an X-ray imaging apparatus. The configuration of this apparatus represents one example of the present invention relating to the X-ray imaging apparatus.

As shown in FIG. 1, the present apparatus includes an X-ray irradiating device 200 and an X-ray detecting device 400. The X-ray irradiating device 200 is configured such that an X-ray irradiator 220 is attached at the leading end of a column 210 hanging from a ceiling. The X-ray irradiator 220 is one example of an X-ray irradiator in the present invention.

The X-ray irradiator 220 can change its direction so as to change the irradiation direction of the X-ray. The column 210 supporting the X-ray irradiator 220 is extendable and retractable in the longitudinal direction, and movable in the horizontal direction along the ceiling.

The X-ray detecting device 400 is configured such that a carriage 420 is attached to a column 410, which stands upright on the floor, so as to be capable of moving up and down, and an X-ray detector 440 is attached to the leading end of an arm 430 of the carriage 420. The column 410 is one example of a column in the present invention. The X-ray detecting device 400 is an X-ray detecting means of a so-called wall stand type. The X-ray detecting device 400 is sometimes referred to as an X-ray detecting stand below.

The X-ray detector 440 has a plate-like structure, wherein the direction thereof is changeable in order that the X-ray incident surface becomes vertical or horizontal according to the incident direction of the X-ray. The X-ray detector 440 is one example of an X-ray detector in the present invention.

The detection signal of the X-ray detector 440 is inputted to an operator console 600. The operator console 600 reconstructs the fluoroscopic image, which is a subject to be imaged, on the basis of the input signal from the X-ray detector 440, and displays the reconstructed image on a display 610.

The operator console 600 controls the X-ray irradiating device 200 and the X-ray detecting device 400 under the operation by an operator. The operator console 600 controls the position of the X-ray irradiator 220 of the X-ray irradiating device 200 in the horizontal and vertical direction, and further controls the X-ray intensity and irradiation timing thereof. The operator console 600 controls the height of the X-ray detector 440 of the X-ray detecting device 400 according to the X-ray irradiator 220, and further controls its posture so as to become vertical or horizontal according to the X-ray incident direction.

Figure 2:
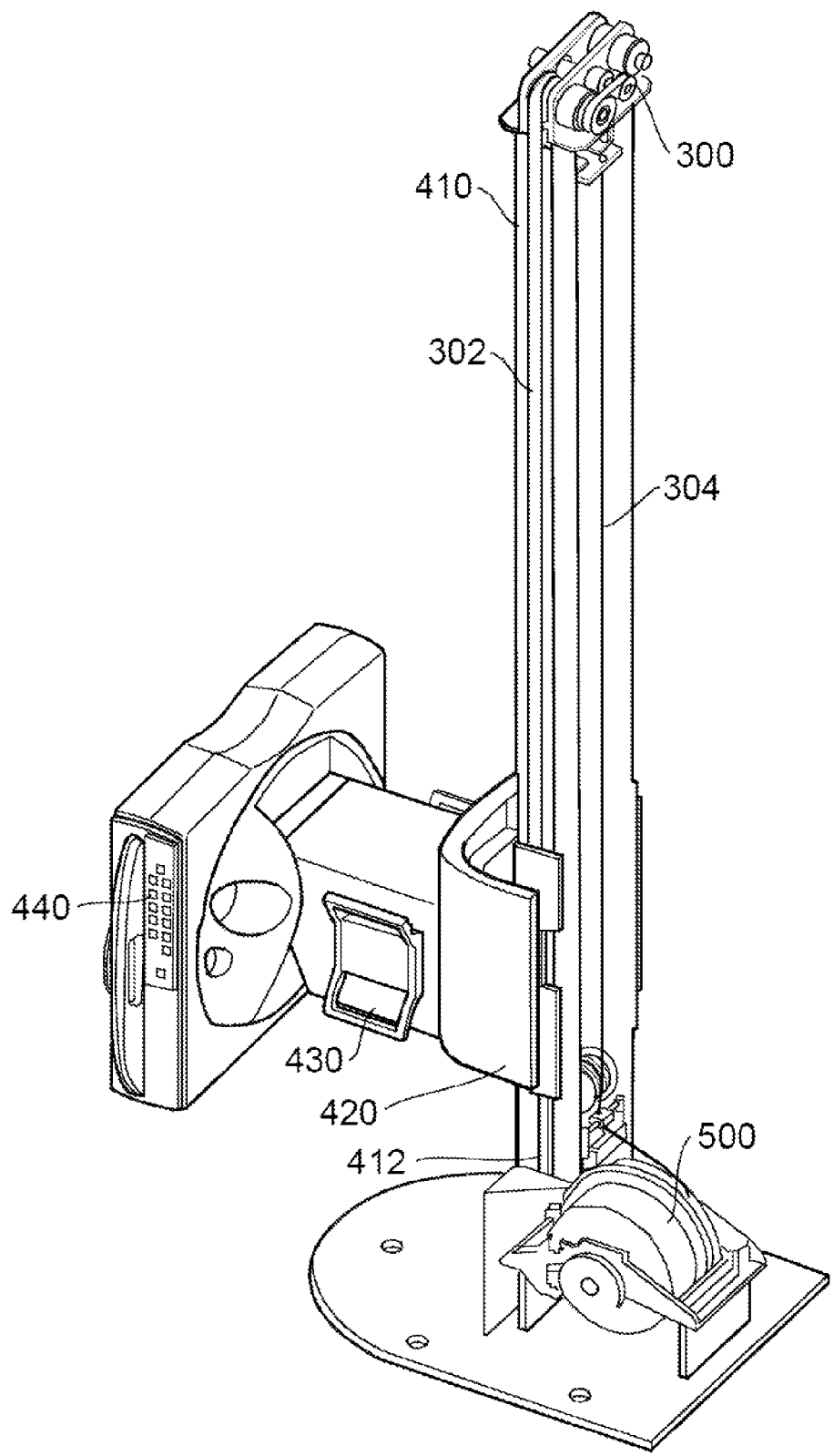
FIG. 2 is a view showing a configuration of an X-ray detecting stand according to one example of the best mode for carrying out the present invention.

FIG. 2 shows one example of the configuration of the X-ray detecting stand 400. The X-ray detecting stand 400 is one example of a best mode for carrying out the present invention. One example of the best mode for carrying out the present invention relating to the X-ray stand is illustrated by the configuration of the X-ray detecting stand 400.

As shown in FIG. 2, the column 410 has a rail 412 extending vertically along the side face. The rail 412 is provided at both side faces of the column 410, and the carriage 420 can move up and down along the rail 412.

The carriage 420 is driven by a motor 300, provided at the upper part of the column 410, through a belt 302. The belt 302 hangs down along the both side faces of the belt 302. The motor 300 is one example of elevating device in the present invention. The belt 302 is one example of a belt in the present invention. It is to be noted that the carriage 420 can manually be raised and lowered.

Tension is applied to the end portion of the belt 302 opposite to the carriage 420 from a balancing mechanism 500 through an inextensible wire 304 such as, for example, a steel wire. The balancing mechanism 500 is provided at the lower part of the column 410. The tension is set so as to balance the total weight from the carriage 420 to the X-ray detector 440. The balancing mechanism 500 is one example of a balancing mechanism in the present invention.

Figure 3:
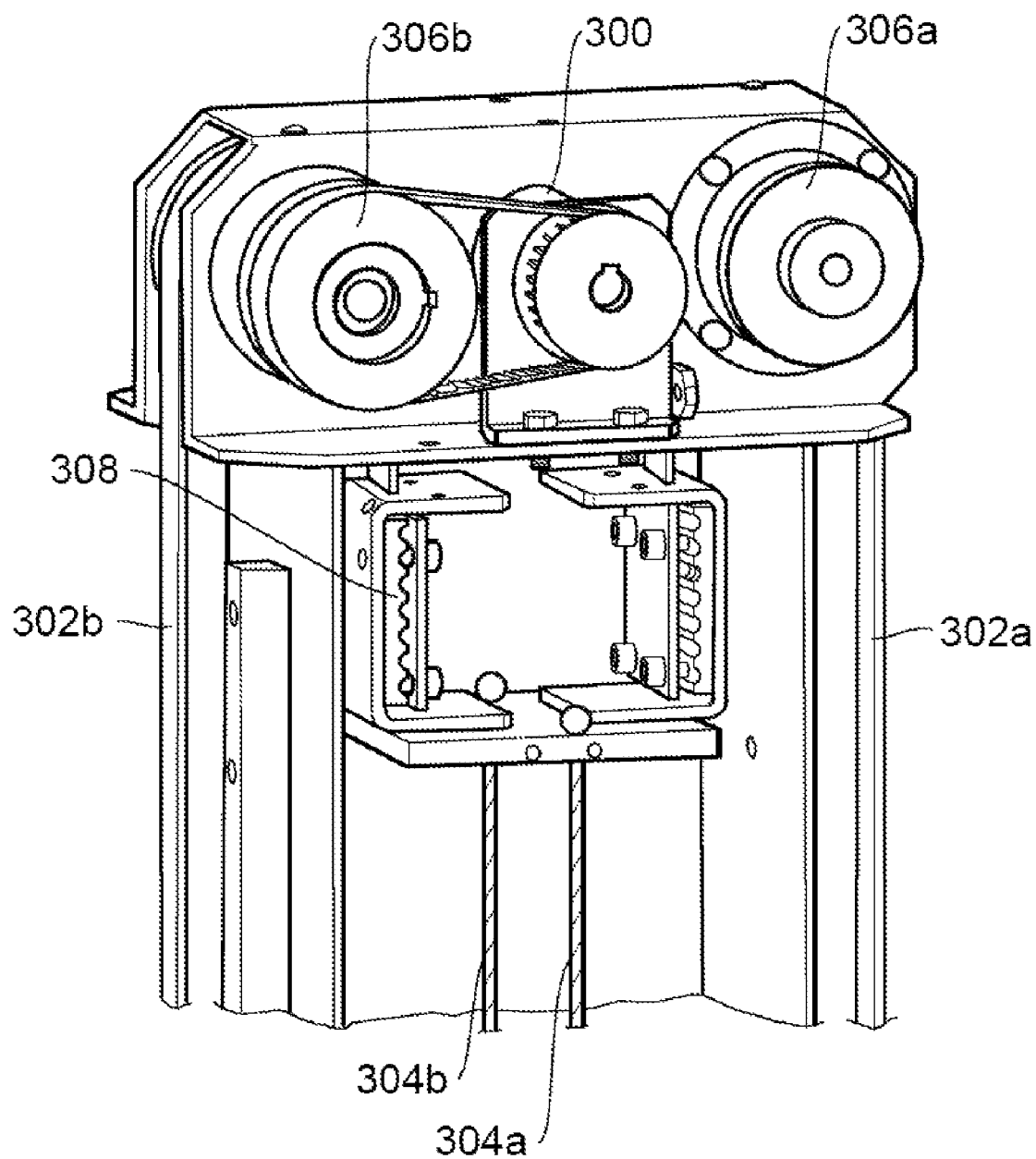
FIG. 3 is a view showing an upper structure of a column.

FIG. 3 shows an upper structure of the column 410. As shown in FIG. 3, a pair of pulleys 306a and 306b, which are driven by the motor 300, is provided at the upper part of the column 410 so as to be symmetrical, and these pulleys 306a and 306b drive a pair of belts 302a and 302b respectively. The driving direction of the pulleys 306a and 306b by the motor 300 is reverse to each other.

One end of each of the belts 302a and 302b is fixed to the carriage 420 at the outside of the column 410, and the other end thereof is fixed to a belt mount 308 at the inside of the column 410.

One end of each of wires 304a and 304b is fixed to the belt mount 308. The wires 304a and 304b are, for example, inextensible wires such as steel wires. The wire 304a is one example of a first wire in the present invention. The wire 304b is one example of a second wire in the present invention.

Figure 4:
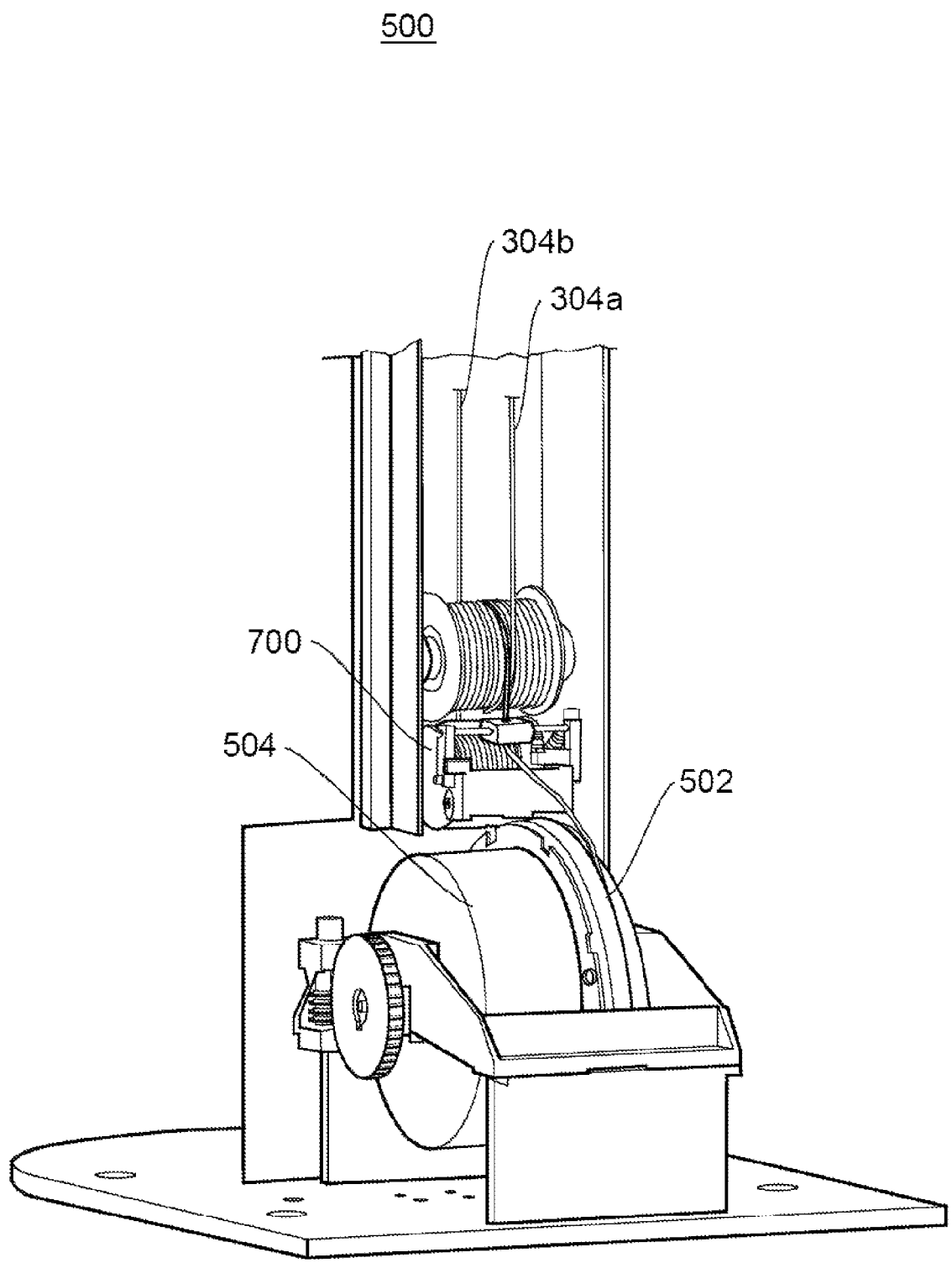
FIG. 4 is a view showing a lower structure of a column.

FIG. 4 shows a lower structure of the column 410. As shown in FIG. 4, the balancing mechanism 500 has a tower wheel 502 that rolls up the other end of the wire 304a. The tower wheel 502 is one example of a first wheel in the present invention.

Take-up torque is generated by an unillustrated clockwork spring provided at the inside of a spring box 504. This take-up torque gives tension to the wire 304a. The torque of the clockwork spring is set such that the tension balances the total weight from the carriage 420 to the X-ray detector 440. The clockwork spring in the spring box 504 is one example of a first spring in the present invention.

Accordingly, the load upon raising and lowering the carriage is reduced. Specifically, the balancing action can be realized without using a counterpoise. The balancing mechanism 500 can be downsized, so that it can be reduced more than the volume of a counterpoise made of lead. Therefore, the elevating range of the X-ray detector 440 can be increased, supposing that the length of the column 410 is the same.

The balancing mechanism 500 includes a safety mechanism 700. The safety mechanism 700 is provided at the upstream side of the tower wheel 502. The wire 304a is reeled up by the tower wheel 502 through the safety mechanism 700.

Figure 5:
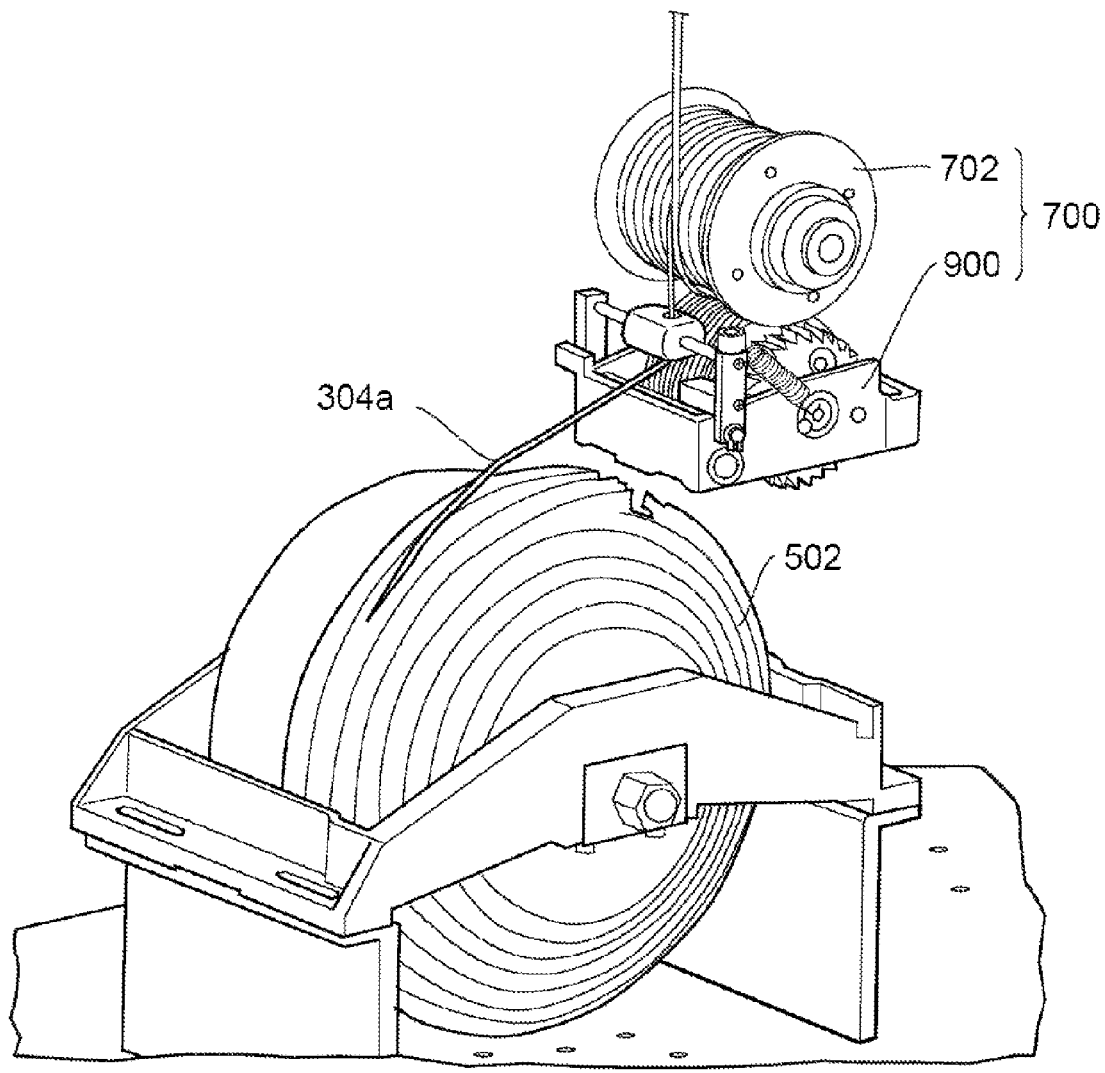
FIG. 5 is a view showing a configuration of a safety mechanism.

FIG. 5 shows the configuration of the safety mechanism 700. As shown in FIG. 5, the safety mechanism 700 has a rotatable transition wheel 702 and a ratchet mechanism 900. After reeled up by the transition wheel 702, the wire 304a is reeled up by the tower wheel 502 through the ratchet mechanism 900. The transition wheel 702 is one example of a transition wheel in the present invention.

Figure 6:
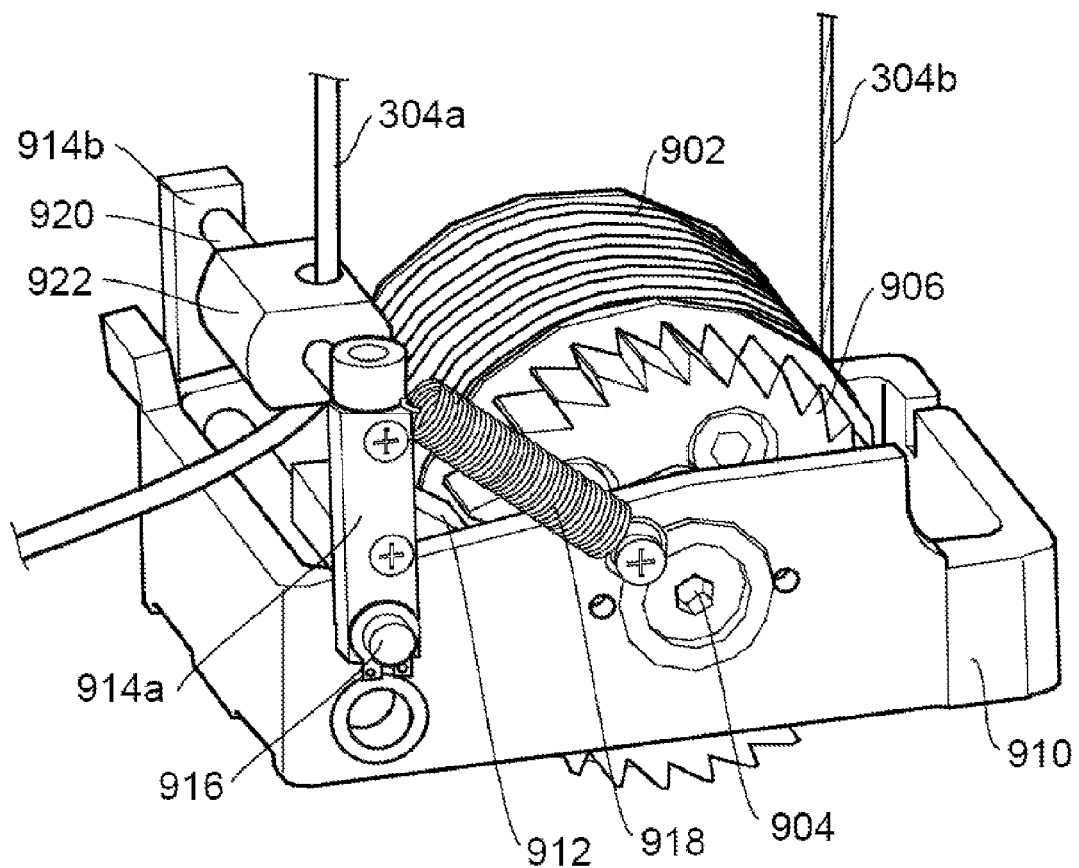
FIG. 6 is a view showing a configuration of a ratchet mechanism.

FIG. 6 shows the configuration of the ratchet mechanism 900. As shown in FIG. 6, the ratchet mechanism 900 includes a safety wheel 902. The safety wheel 902 is one example of a second wheel in the present invention.

The other end of the wire 304b is reeled up by the safety wheel 902. The take-up torque of the wire 304b is produced by an unillustrated clockwork spring provided at the inside of the safety wheel 902. The clockwork spring in the safety wheel 902 is one example of a second clockwork spring in the present invention.

One end of the clockwork spring is coupled to the inner wall of the safety wheel 902, while the other end thereof is coupled to a center axis 904, in the safety wheel 902. A ratchet gear 906 whose rotational shaft is the center axis 904 is fixed to the center axis 904. The center axis 904 is attached so as to be rotatable at a bracket 910. The center axis 904 is one example of an axis in the present invention. The ratchet gear 906 is one example of a ratchet gear in the present invention.

A detent 912 is formed so as to correspond to the ratchet gear 906. The detent 912 is mounted to a swing arm 914a. The swing arm 914a is mounted swingable to the bracket 901 about an axis 916. A spring 918 applies to the swing arm 914a force for throwing down the swing arm 914a toward the ratchet gear 906.

The detent 912 is one example of a detent in the present invention. The swing arm 914a is one example of a swing arm in the present invention. The spring 918 is one example of a spring in the present invention.

A swing arm 914b is provided at the opposite side of the bracket 910 so as to be swingable about the axis 916. The leading ends of the swing arms 914a and 914b are linked to each other by a common lateral shaft 920.

A detent wheel 922 is rotatably provided to the lateral shaft 920. The wire 304a is put around the detent wheel 922. Tension is applied to the wire 304a by the take-up torque of the tower wheel 502, and the swing arm 914a is returned against the force of the spring 918 by this tension. Therefore, the engagement between the detent 912 and the ratchet gear 906 is prevented.

A mechanism composed of the swing arms 914a and 914b, the axis 916, the lateral shaft 920, the detent wheel 922, and the wire 304a put around the detent wheel 922 is one example of a preventing mechanism in the present invention. Further, it is one example of a returning mechanism in the present invention.

The transition wheel 702 is provided at the upstream side of the position very close to the detent wheel 922. The wire 304a is completely reeled up by the transition wheel 702, and then, put around the detent wheel 922 from the vertical direction, whereby the swing arm 914a can effectively be returned by the tension of the wire 304a.

During when this state is maintained, the ratchet gear 906 is in a free state. Therefore, the clockwork spring in the safety wheel 902 are not involved with the generation of balancing force, and only the take-up torque of the tower wheel 502 is involved with the generation of the balancing force. Specifically, only the balancing mechanism 500 performs the balancing operation, and the ratchet mechanism 900 does not perform the balancing operation.

When the wire 304a is broken by some causes, the balancing operation by the balancing mechanism 500 is lost. In this case, the tension of the wire 304a is eliminated, so that the swing arm 914a is thrown down toward the ratchet gear 906 by the force of the spring 918, whereby the detent 912 is engaged with the ratchet gear 906. Thus, the rotation of the ratchet gear 906 is locked.

Since the ratchet gear 906 is locked, the ratchet mechanism 900 generates balancing force by the torque of the clockwork spring in the safety wheel 902. In this manner, the backup of the balancing operation is performed, even if the wire 304a is broken, whereby safety is maintained.

What is claimed is:

1. An X-ray detecting stand, comprising:
   an X-ray detector;
   a vertical column configured to support said X-ray detector so as to be movable;
   an elevating device configured to raise and lower said X-ray detector along said column through a belt; and
   a balancing mechanism configured to exert force, which balances a load by said X-ray detector, to said belt by a first clockwork spring.

2. An X-ray detecting stand according to claim 1, wherein said balancing mechanism comprises:

a first wire having a first end coupled to said belt at a side opposite to said X-ray detector;
a first wheel configured to reel up a second end of said first wire, wherein the first clockwork spring is configured to apply take-up torque to said first wheel.

3. An X-ray detecting stand according to claim 2, wherein said balancing mechanism comprises:
a second wire having a first end coupled to said belt at the side opposite to said X-ray detector;
a second wheel configured to reel up a second end of said second wire;
a second clockwork spring configured to apply take-up torque to said second wheel;
a rotatable axis coupled to an end of said second clockwork spring opposite to said second wheel;
a ratchet gear having an axis as a rotational axis;
a detent that is biased by a third spring toward a direction of engaging with said ratchet gear; and
a preventing mechanism configured to prevent engagement between said detent and said ratchet gear by utilizing tension of said first wire.

4. An X-ray detecting stand according to claim 3, wherein said preventing mechanism comprises:
a swing arm to which said detent is mounted, wherein said third spring is configured to bias said swing arm toward said ratchet gear; and
a returning mechanism configured to return said swing arm toward a direction reverse to said ratchet gear by utilizing the tension of said first wire.

5. An X-ray detecting stand according to claim 4, wherein said returning mechanism comprises a transition wheel configured to regulate a direction of said first wire.

6. An X-ray detecting stand according to claim 1, wherein said balancing mechanism is provided at a lower part of said column.

7. An X-ray detecting stand according to claim 1, wherein said elevating device comprises a driving mechanism configured to drive said belt at an upper part of said column.

8. An X-ray detecting stand according to claim 7, wherein said driving mechanism is configured to raise and lower said X-ray detector through two belts parallel to both side faces of said column.

9. An X-ray imaging apparatus, comprising:
an X-ray detector;
a vertical column configured to support said X-ray detector so as to be movable;
an elevating device configured to raise and lower said X-ray detector along said column through a belt;
an X-ray irradiator; and
a balancing mechanism configured to exert force, which balances a load by said X-ray detector, to said belt by a first clockwork spring.

10. An X-ray imaging apparatus according to claim 9, wherein said balancing mechanism comprises:
a first wire having a first end coupled to said belt at a side opposite to said X-ray detector;
a first wheel configured to reel up a second end of said first wire, wherein said first clockwork spring is configured to apply take-up torque to said first wheel.

11. An X-ray imaging apparatus according to claim 10, wherein said balancing mechanism comprises:
a second wire having a first end coupled to said belt at the side opposite to said X-ray detector;
a second wheel configured to reel up a second end of said second wire;
a second clockwork spring configured to apply take-up torque to said second wheel;
a rotatable axis coupled to an end of said second clockwork spring opposite to said second wheel;
a ratchet gear having an axis as a rotational axis;
a detent that is biased by a third spring toward a direction of engaging with said ratchet gear; and
a preventing mechanism configured to prevent engagement between said detent and said ratchet gear by utilizing tension of said first wire.

12. An X-ray imaging apparatus according to claim 11, wherein said preventing mechanism comprises:
a swing arm to which said detent is mounted, wherein said third spring is configured to bias said swing arm toward said ratchet gear; and
a returning mechanism configured to return said swing arm toward a direction reverse to said ratchet gear by utilizing the tension of said first wire.

13. An X-ray imaging apparatus according to claim 12, wherein said returning mechanism comprises a transition wheel configured to regulate a direction of said first wire.

14. An X-ray imaging apparatus according to claim 9, wherein said balancing mechanism is provided at a lower part of said column.

15. An X-ray imaging apparatus according to claim 9, wherein said elevating device comprises a driving mechanism configured to drive said belt at an upper part of said column.

16. An X-ray imaging apparatus according to claim 15, wherein said driving mechanism is configured to raise and lower said X-ray detector through two belts parallel to both side faces of said column.

17. A method of assembling an X-ray detecting stand, comprising:
movably coupling an X-ray detector to a vertical column;
coupling an elevating device to the column such that the X-ray detector is movable in an upward direction and a downward direction using a belt;
coupling a balancing mechanism to the elevating device, the balancing mechanism configured to exert a force in order to balance the X-ray detector along the column using the belt;
coupling a first end of a first wire to the belt at a side opposite to the X-ray detector;
coupling a first wheel to a second end of the first wire; and
coupling a first clockwork spring to the first wheel, the first clockwork spring configured to apply take-up torque to the first wheel.

18. A method according to claim 17, further comprising:
coupling a first end of a second wire to the belt at a side opposite to the X-ray detector;
coupling a second wheel to a second end of the first wire; and
coupling a second clockwork spring to the second wheel, the second clockwork spring configured to apply take-up torque to the second wheel.

19. A method according to claim 18, further comprising:
coupling a rotatable axis to an end of the second clockwork spring opposite to the second wheel;
coupling a detent to a ratchet gear that is configured to rotate about the rotational axis, the detent biased by a spring toward a direction of engaging with the ratchet gear; and
positioning a preventing mechanism with respect to the detent and the ratchet gear, the preventing mechanism configured to prevent engagement between the detent and the ratchet gear by utilizing tension in the first wire.

* * * * *